United States Patent
Akabane et al.

(10) Patent No.: US 9,951,090 B2
(45) Date of Patent: Apr. 24, 2018

(54) MONO-FUNCTIONAL BRANCHED ORGANOSILOXANE COMPOUND AND METHOD FOR PRODUCING THE SAME

(71) Applicant: SHIN-ETSU CHEMICAL CO., LTD., Tokyo (JP)

(72) Inventors: Emi Akabane, Annaka (JP); Tomoyuki Goto, Annaka (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 0 days.

(21) Appl. No.: 15/270,380

(22) Filed: Sep. 20, 2016

(65) Prior Publication Data

US 2017/0101423 A1    Apr. 13, 2017

(30) Foreign Application Priority Data

Oct. 9, 2015   (JP) ................... 2015-200681

(51) Int. Cl.
    C07F 7/08    (2006.01)
(52) U.S. Cl.
    CPC ................. C07F 7/0889 (2013.01)
(58) Field of Classification Search
    USPC ...................... 556/446, 450, 451
    See application file for complete search history.

(56) References Cited

U.S. PATENT DOCUMENTS

| | | | |
|---|---|---|---|
| 5,045,621 A | 9/1991 | Suzuki | |
| 6,306,992 B1 | 10/2001 | Yoshitake et al. | |
| 6,420,504 B1 | 7/2002 | Yoshitake et al. | |
| 2004/0242912 A1 | 12/2004 | Kubota et al. | |

FOREIGN PATENT DOCUMENTS

| | | |
|---|---|---|
| JP | S59-78236 A | 5/1984 |
| JP | 2842443 B2 | 1/1999 |
| JP | 4236342 B2 | 3/2009 |
| JP | 4270593 B2 | 6/2009 |
| JP | 4305635 B2 | 7/2009 |

OTHER PUBLICATIONS

Hreczycho; New Journal of Chemistry; 2011, 35, 2743-2746.*
Popowski (Organosilicon Chemistry IV: From molecules to Materials; Reactions of siloxysilanes with alkali metal trimethylsilanolates; Jun. 10, 2008; 424-429).*
Hreczycho et al., "A New Selective Approach to Unsymmetrical Siloxanes and Germasiloxanes via O-metalation of Silanols with 2-methylallylsilanes and 2-methylallylgermanes", New Journal of Chemistry, vol. 35, No. 12, pp. 2743-2746, 2011.
Hreczycho., "An Efficient Catalytic Approach for the Synthesis of Unsymmetrical Siloxanes", European Journal of Inorganic Chemistry, vol. 1, pp. 67-72, 2015.
Mar. 7, 2017 Search Report issued in European Patent Application No. 16002076.4.
Grzegorz Hreczycho; "An Efficient Catalytic Approach for the Synthesis of Unsymmetrical Siloxanes;" European Journal of Inorganic Chemistry—Chemische Berichte; vol. 2015, No. 1; Nov. 27, 2014; pp. 67-72; p. 69, table 1, compound 4.
H. Jancke et al.; "29SI-NMR-Spektroskopische Untersuchungen an Funktionalisierten Siloxanen" Journal of Organometallic Chemistry, Elsevier-Sequoia S.A. Lausanne, CH; vol. 354; Jan. 1, 1998; pp. 23-29; p. 25, table 1, compound 5.
Joachim Schulz et al.; Silicon-hydrogen stretching vibrations and silicon-29-proton-coupling constants of siloxysilanes: Zeitschrift Fuer Chemie; 1998; p. 68; table 1; compunds 5, 11.
E. Popowski et al., "Darstellung and Ir-spelctroskopische Untersuchungen von Siloxysilanolen;" Z. Anorg. Allg. Chem.; vol. 494, Jan. 1, 1982; pp. 166-178; compound 4, table 4, p. 176.

* cited by examiner

*Primary Examiner* — Pancham Bakshi
(74) *Attorney, Agent, or Firm* — Oliff PLC

(57) ABSTRACT

The present invention is a mono-functional branched organosiloxane compound that is liquid and shown by the following general formula (1)

$$M_{a-1}M^R_{a-2}D_{b-1}D^R_{b-2}T_{c-1}T^R_{c-2}Q_{d-1} \quad (1)$$

wherein $M=R^1_3SiO_{0.5}$, $M^R=R^1_2R^2SiO_{0.5}$, $D=R^1_2SiO$, $D^R=R^2R^1SiO$, $T=R^1SiO_{1.5}$, $T^R=R^2SiO_{1.5}$, and $Q=SiO_2$, where $R^1$ represents a group selected from an alkyl group having 1 to 30 carbon atoms, and so on, $R^2$ represents a hydrogen atom, and so on, a-1 represents an integer of 1 or more, b-1 and c-1 each represent an integer of 0 or more, and a-2, b-2, c-2, and d-1 each represent 0 or 1, provided that c-1, c-2, and d-1 are not simultaneously 0, a total of a-2, b-2, and c-2 is 1, and when b-1 is 0, a-1 is 2 or more and a total of c-1 and d-1 is 1 or more. There can be provided a novel mono-functional branched organosiloxane compound having a branched structure, and a method for producing the same.

2 Claims, No Drawings

MONO-FUNCTIONAL BRANCHED ORGANOSILOXANE COMPOUND AND METHOD FOR PRODUCING THE SAME

TECHNICAL FIELD

The present invention relates to a novel mono-functional branched organosiloxane compound having a branched structure, and a method for selectively producing the novel mono-functional branched organosiloxane compound.

BACKGROUND ART

An organosiloxane having a functional group at one terminal of its molecular chain is used as a raw material of a graft organic polymer that has organosiloxane chain branches by reactivity of the functional group. The organic polymer incorporating this organosiloxane has high functions such as powder dispersibility, water repellency, antifouling property, non-adhesiveness, heat resistance, wear resistance, biocompatibility, and oxygen permeability.

It is conventionally known that the organosiloxane having a functional group at one terminal of its molecular chain can be synthesized by ring-opening polymerization of hexamethylcyclotrisiloxane, followed by capping the reaction terminal with terminating agents containing various functional groups (Patent Literature 1 and Patent Literature 2).

It is also known that an organosiloxane having a (meth) acryl group at one terminal can be synthesized by ring-opening polymerization of hexamethylcyclotrisiloxane using trimethyl silanol or 3-methacryloxypropyldimethyl silanol as an initiator in the presence of 5-coordinate silicon catalyst, followed by terminating the reaction by 3-methacryloxypropyldimethylchlorosilane or trimethylchlorosilane.

In the above method, however, the organosiloxane of the main chain is not branched and has inadequate oxygen permeability, sliding property, release property, dispersibility, and so on.

A method for synthesizing a branched siloxane is proposed in Patent Literature 3, which discloses a method for producing a branched tetrasiloxane in high yield by hydrolysis reaction in the presence of an acid catalyst. However, a method for polymerizing the siloxane has not been disclosed. Synthesis methods reported by Hrecaycho and others enable a target product to be obtained in high yield, but require a specific catalyst (Non Patent Literatures 1 and 2).

Patent Literature 4 and Patent Literature 5 propose compounds having a dendrimer structure, which are one-molecular-chain-terminal functionalized organosiloxane compounds having an extremely branched organosiloxane chain. A material using this compound is excellent in coating property, but a method for producing the same requires complicated steps and a specific starting material for synthesis.

CITATION LIST

Patent Literature

Patent Literature 1: Japanese Unexamined Patent publication (Kokai) No. S59-78236
Patent Literature 2: Japanese Patent No. 2842443
Patent Literature 3: Japanese Patent No. 4305635
Patent Literature 4: Japanese Patent No. 4236342
Patent Literature 5: Japanese Patent No. 4270593

Non Patent Literature

Non Patent Literature 1: New Journal of Chemistry (2011), 35 (12), 2743-2746
Non Patent Literature 2: European Journal of Inorganic Chemistry (2015), 2015 (1), 67-72

SUMMARY OF INVENTION

Technical Problem

The present invention was accomplished in view of the above-described circumstances. It is an object of the present invention to provide a novel mono-functional branched organosiloxane compound having a branched structure, and a method for producing the same.

Solution to Problem

To achieve this object, the present invention provides a mono-functional branched organosiloxane compound that is liquid and shown by the following general formula (1)

$$M_{a-1}M^R_{a-2}D_{b-1}D^R_{b-2}T_{c-1}T^R_{c-2}Q_{d-1} \quad (1)$$

wherein $M=R^1_3SiO_{0.5}$, $M^R=R^1_2R^2SiO_{0.5}$, $D=R^1_2SiO$, $D^R=R^2R^1SiO$, $T=R^1SiO_{1.5}$, $T^R=R^2SiO_{1.5}$, and $Q=SiO_2$, where $R^1$ may be different from each other and represents a group selected from an alkyl group, an aryl group, an aralkyl group, and a fluorinated alkyl group having 1 to 30 carbon atoms, $R^2$ represents a hydrogen atom or a group selected from a hydroxyl group, a group containing a mercapto group, and a group containing a polymerizable unsaturated group, a-1 represents an integer of 1 or more, b-1 and c-1 each represent an integer of 0 or more, and a-2, b-2, c-2, and d-1 each represent 0 or 1, provided that c-1, c-2, and d-1 are not simultaneously 0, a total of a-2, b-2, and c-2 is 1, and when b-1 is 0, a-1 is 2 or more and a total of c-1 and d-1 is 1 or more.

The inventive mono-functional branched organosiloxane compound has good reactivity and is useful as a silicone material for modifying an organic resin or an intermediate material for producing a highly functional silicone.

c-2 is preferably 0 in the general formula (1).

a-2 is preferably 1 in the general formula (1).

Such a mono-functional branched organosiloxane compound has little steric hindrance and particularly high reactivity.

Furthermore, the present invention provides a method for producing a mono-functional branched organosiloxane compound, comprising reacting an organosiloxane containing one silanol group per molecule with an organic chlorosilane compound in the presence of a base to selectively obtain the inventive mono-functional branched organosiloxane compound.

The inventive producing method is simple, convenient, and high yield, and thus can effectively produce the inventive mono-functional branched organosiloxane compound.

The organosiloxane containing one silanol group per molecule is preferably obtained by a reaction of an organohydrogensiloxane with water in the presence of a catalyst.

The organosiloxane containing one silanol group per molecule can be produced in high yield by such reaction. Accordingly, the method using the organosiloxane containing one silanol group per molecule thus obtained to produce a mono-functional branched organosiloxane compound enables the mono-functional branched organosiloxane compound to be produced at low cost.

The organohydrogensiloxane is preferably any of 1,1,1,3,3-pentamethyldisiloxane, 1,1,1,3,5,5,5-heptamethyltrisiloxane, tris(trimethylsiloxy)silane, 1,1,1,3,3,5,5,7,7,9,9-undecamethylpentasiloxane, and 1-butyl-1,1,3,3,5,5,7,7,9,9-decamethylpentasiloxane.

Such organohydrogensiloxanes are easily available and can be easily produced. Thus, the organosiloxane containing one silanol group per molecule can be easily produced by using these compounds. Accordingly, the method using the organosiloxane containing one silanol group per molecule thus obtained to produce a mono-functional branched organosiloxane compound enables the mono-functional branched organosiloxane compound to be more easily produced.

The organic chlorosilane compound is preferably any of dimethylchlorosilane, methyldichlorosilane, trichlorosilane, methylphenylchlorosilane, phenyldichlorosilane, dimethylvinylchlorosilane, allylmethyldichlorosilane, allyldimethylchlorosilane, allyltrichlorosilane, methylphenylvinylchlorosilane, allylphenyldichlorosilane, phenylvinyldichlorosilane, diphenylchlorosilane, diphenylvinylchlorosilane, 3-methacryloxypropyldimethylchlorosilane, 3-methacryloxypropyldichloromethylsilane, and 3-mercaptopropyltrichlorosilane.

Such organic chlorosilane compounds are commercially and easily available. Thus, the mono-functional branched organosiloxane compound can be still more easily produced by using these compounds.

Advantageous Effects of Invention

The inventive mono-functional branched organosiloxane compound has good reactivity and is useful as a silicone material for modifying an organic resin or an intermediate material for producing a highly functional silicone. In addition, the inventive producing method is simple, convenient, and high yield. Thus this method can effectively produce the inventive mono-functional branched organosiloxane compound.

DESCRIPTION OF EMBODIMENTS

Hereinafter, the present invention will be described in detail.

As described previously, there are demands for a novel mono-functional branched organosiloxane compound having a branched structure, and a method for producing the same.

The present inventors have earnestly investigated to accomplish the above object. Consequently, they found that a mono-functional branched organosiloxane compound that is liquid and shown by the general formula (1) can accomplish the object, and the inventive producing method enables high yield production of this compound, thereby bringing the present invention to completion.

Hereinafter, embodiments of the present invention will be described specifically, but the present invention is not limited thereto.

The inventive mono-functional branched organosiloxane compound, which is shown by the following general formula (1), is liquid, contains one functional group, and has a branched structure. Such a compound has good reactivity and useful as a silicone material for modifying an organic resin or an intermediate material for producing a highly functional silicone.

$$M_{a\text{-}1}M^R_{a\text{-}2}D_{b\text{-}1}D^R_{b\text{-}2}T_{c\text{-}1}T^R_{c\text{-}2}Q_{d\text{-}1} \quad (1)$$

wherein $M=R^1_3SiO_{0.5}$, $M^R=R^1_2R^2SiO_{0.5}$, $D=R^1_2SiO$, $D^R=R^2R^1SiO$, $T=R^1SiO_{1.5}$, $T^R=R^2SiO_{1.5}$, and $Q=SiO_2$, where $R^1$ may be different from each other and represents a group selected from an alkyl group, an aryl group, an aralkyl group, and a fluorinated alkyl group having 1 to 30 carbon atoms, $R^2$ represents a hydrogen atom or a group selected from a hydroxyl group, a group containing a mercapto group, and a group containing a polymerizable unsaturated group, a-1 represents an integer of 1 or more, b-1 and c-1 each represent an integer of 0 or more, and a-2, b-2, c-2, and d-1 each represent 0 or 1, provided that c-1, c-2, and d-1 are not simultaneously 0, a total of a-2, b-2, and c-2 is 1, and when b-1 is 0, a-1 is 2 or more and a total of c-1 and d-1 is 1 or more.

Examples of the alkyl group represented by $R^1$ include a methyl group, an ethyl group, a propyl group, an isopropyl group, a butyl group, an isobutyl group, a tert-butyl group, a pentyl group, a neopentyl group, a hexyl group, a heptyl group, an octyl group, a nonyl group, a decyl group, and dodecyl group; typically, a methyl group, an ethyl group, a propyl group, an isopropyl group, a butyl group, a hexyl group, and an octyl group. In particular, a methyl group is preferable.

Examples of the aryl group represented by $R^1$ include a phenyl group, a tolyl group, a xylyl group, and a naphthyl group. Among them, a phenyl group is particularly preferable.

Examples of the aralkyl group represented by $R^1$ include a benzyl group, a phenylethyl group, a phenylpropyl group, and a methylbenzyl group; a benzyl group and a phenylpropyl group are preferable.

Examples of the fluorinated alkyl group represented by $R^1$ include 3,3,3-trifluoropropyl group and 3,3,4,4,5,5,6,6,6-nonafluorohexyl group.

$R^1$ may be different from each other.

Examples of the group containing a mercapto group represented by $R^2$ include a mercapto group, a mercaptomethyl group, a mercaptoethyl group, and a mercaptopropyl group.

The group containing a polymerizable unsaturated group represented by $R^2$ is preferably a structure shown by the following formula (2), $$-(CH_2)_e-(OCO)_f C(R^3)=CH_2 \quad (2)$$

wherein $R^3$ represents a hydrogen atom, a linear or branched alkyl group having 1 to 6 carbon atoms, or an aryl group having 6 to 12 carbon atoms, "e" represents an integer of 0 to 10, "f" represents 0 or 1, provided that when "f" is 1, "e" is 1 to 10.

In the formula (2), $R^3$ represents a hydrogen atom, a linear or branched alkyl group having 1 to 6 carbon atoms, or an aryl group having 6 to 12 carbon atoms. Examples of the linear or branched alkyl group include a methyl group, an ethyl group, a propyl group, an isopropyl group, a butyl group, an isobutyl group, a tert-butyl group, a pentyl group, a neopentyl group, and a hexyl group. Examples of the aryl group include a phenyl group, a tolyl group, and a xylyl group. $R^3$ is preferably a hydrogen atom or a methyl group.

"e" represents an integer of 0 to 10, particularly preferably an integer of 0 to 5. "f" represents 0 or 1. However, when "f" is 1, "e" is an integer of 1 to 10, particularly preferably an integer of 2 to 5.

a-1, b-1, and c-1 are as described above. Specifically, a-1 represents an integer of 1 or more, preferably an integer of 1 to 200, more preferably an integer of 1 to 100. b-1 represents an integer of 0 or more, preferably an integer of 0 to 500, more preferably an integer of 1 to 200. c-1 represents an integer of 0 or more, preferably an integer of 0 to 100, more preferably an integer of 1 to 50. d-1 represents 0 or 1, preferably 1.

As described above, a-2, b-2, and c-2 each represent 0 or 1. However, when b-1 is 0, a-1 should be 2 or more and the total of c-1 and d-1 should be 1 or more so as to achieve a branched structure with high functionality. Moreover, c-1, c-2, and d-1 are not simultaneously 0. To obtain a mono-functional compound, the total of a-2, b-2, and c-2 is 1, and the compound preferably satisfies c-2-0, more preferably a-2-1. When particularly high reactivity is required, the compound preferably satisfies a-2=1 or b-2=1, particularly a-2=1, for such a compound has less steric hindrance.

The mono-functional branched organosiloxane compound shown by the general formula (1) is liquid, that is, shows flowability at room temperature. More specifically, the definition of liquid is as follows: A test tube (a flat-bottomed cylindrical vessel made of transparent glass, having an inner diameter of 30 mm and a height of 120 mm) having labelled lines at heights of 55 mm [A-line] and 85 mm [B-line] from the bottom is prepared. A specimen is poured into the test tube up to A-line, and the test tube is laid at 20±5° C. When the specimen flows over B-line within 90 seconds, this fluid is defined as liquid.

Next, the inventive method for producing a mono-functional branched organosiloxane compound will be described. The inventive method for producing a mono-functional branched organosiloxane compound includes reacting an organosiloxane containing one silanol group per molecule with an organic chlorosilane compound in the presence of a base to selectively obtain the inventive mono-functional branched organosiloxane compound. Such a producing method is simple, convenient, and high yield. Thus, this method can effectively produce the inventive mono-functional branched organosiloxane compound. The method will be described more specifically below.

[Step 1]

The organosiloxane containing one silanol group per molecule can be obtained by a reaction of an organohydrogensiloxane with water in the presence of a catalyst. Such a reaction enables the organosiloxane containing one silanol group per molecule to be produced in high yield. Examples of the organohydrogensiloxane used in [Step 1] include a compound shown by the following general formula (3),

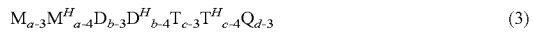

wherein $M=R^1_3SiO_{0.5}$, $M^H=R^1_2HSiO_{0.5}$, $D=R^1_2SiO$, $D^H=HR^1SiO$, $T=R^1SiO_{1.5}$, $T^H=HSiO_{1.5}$, and $Q=SiO_2$ where $R^1$ is as defined above, a-3 represents an integer of 1 or more, b-3 and c-3 each represent an integer of 0 or more, and a-4, b-4, c-4, and d-3 each represent 0 or 1, provided that a total of a-4, b-4, and c-4 is 1.

Illustrative examples of the organohydrogensiloxane include 1,1,1,3,3-pentamethyldisiloxane, 1,1,1,3,5,5,5-heptamethyltrisiloxane, tris(trimethylsiloxy)silane, 1,1,1,3,3,5,5,7,7,9,9-undecamethylpentasiloxane, and 1-butyl-1,1,3,3,5,5,7,7,9,9-decamethylpentasiloxane. Such organohydrogensiloxanes are easily available and can be easily produced.

Examples of a method of producing the organohydrogensiloxanes shown by the general formula (3) include, as already known, hydrolysis condensation and living polymerization of an organic silicon compound having a SiH group with an organic silicon compound having an alkyl group. If necessary, purification treatment such as distillation may be performed.

Examples of the catalyst used in [Step 1] include transition metal catalysts and Lewis acid catalysts. Examples of the transition metal catalyst include a ruthenium catalyst, a rhodium catalyst, a palladium catalyst, an iridium catalyst, a platinum catalyst, and a gold catalyst. In particular, a palladium catalyst is preferable. Examples of the Lewis acid catalyst include aluminum chloride, aluminum sulfate, stannic chloride, stannic chloride sulfate, ferric chloride, boron trifluoride, and pentafluorophenyl boron. In particular, pentafluorophenyl boron is preferable.

In [Step 1], a solvent may be used if necessary. The solvent is not particularly limited so long as it is not reactive with raw materials such as the organohydrogensiloxane used in [Step 1], the catalyst, and the organic silicon compound having a Si—H group. Illustrative examples thereof include aliphatic hydrocarbon solvents such as pentane, hexane, heptane, and decane; aromatic hydrocarbon solvents such as benzene, toluene, and xylene; and ether solvents such as diethyl ether, tetrahydrofuran, and 1,4-dioxane.

When the organosiloxane containing one silanol group per molecule is produced in [Step 1], a blending ratio of the organohydrogensiloxane and the catalyst used in [Step 1] is not particularly limited. In view of reactivity and productivity, the reaction is preferably performed with the catalyst in an amount of 0.000001 to 0.1 mol, particularly 0.000001 to 0.01 with respect to 1 mol of the organohydrogensiloxane used in [Step 1]. An amount of 0.000001 or more prevents the reaction speed from decreasing, resulting in a short reaction time. An amount of 0.1 or less prevents yield reduction due to polymerization caused by redistribution reaction of a reaction product, namely, the organosiloxane containing one silanol group per molecule.

When the organosiloxane containing one silanol group per molecule is produced in [Step 1], a blending ratio of the organohydrogensiloxane and water used in [Step 1] is not particularly limited. In view of reactivity and productivity, the reaction is preferably performed with water in an amount of 1 to 5 mol, particularly 1.05 to 3.0 mol with respect to 1 mol of the organohydrogensiloxane used in [Step 1]. An amount of 1 mol or more brings the reaction to completion, enabling a sufficient yield. An amount of 5 mol or less improves yield improvement and enables a sufficient pot yield.

The reaction temperature in [Step 1] preferably ranges from 1° C. to 70° C., particularly 5° C. to 40° C. The reaction time preferably ranges from 30 minutes to 10 hours, particularly 1 hour to 8 hours, although depending on the degree of reaction progress. If necessary, purification treatment such as distillation may be performed, under normal pressure or reduced pressed according to a usual method.

[Step 2]

In [Step 2], the organosiloxane containing one silanol group per molecule obtained in [Step 1] is brought to react with an organic chlorosilane compound in the presence of a base.

The base required as a raw material in [Step 2] is not particularly limited. Illustrative examples thereof include amine-type base such as sodium carbonate, pyridine, triethylamine, ammonia, methylamine, ethylamine, dimethylamine, N-hexylamine, N-ethyldiisopropylamine, imidazole, and N-methylimidazole.

The organic chlorosilane compound used as a raw material is not particularly limited. Examples of the compound that is commercially and easily available include dimethylchlorosilane, methyldichlorosilane, trichlorosilane, methylphenylchlorosilane, phenyldichlorosilane, dimethylvinylchlorosilane, allylmethyldichlorosilane, allyldimethylchlorosilane, allyltrichlorosilane, methylphenylvinylchlorosilane, allylphenyldichlorosilane, phenylvinyldichlorosilane, diphenylchlorosilane, diphenylvinylchlorosilane, 3-methacryloxypropyldimethylchlorosilane, 3-methacryloxypropyldichloromethylsilane, and 3-mercaptopropyltrichlorosilane.

In [Step 2], a solvent may be used if necessary. The solvent is not particularly limited so long as it is not reactive with raw materials such as the organosiloxane obtained in [Step 1], the base, and the organic chlorosilane compound. Illustrative examples thereof include aliphatic hydrocarbon solvents such as pentane, hexane, heptane, and decane; aromatic hydrocarbon solvents such as benzene, toluene, and xylene and; ether solvents such as diethyl ether, tetrahydrofuran, and 1,4-dioxane.

When the inventive mono-functional branched organosiloxane compound is produced, a blending ratio of the organosiloxane (the organosiloxane containing one silanol group per molecule) obtained in [Step 1] and the organic chlorosilane compound is not particularly limited. In view of reactivity and productivity, the reaction is preferably performed such that the amount of Si—Cl groups in the organic chlorosilane compound ranges from 0.01 to 2.0 mol, particularly 0.4 to 1.2 mol with respect to 1 mol of the organosiloxane containing one silanol group per molecule obtained in [Step 1]. An amount of 0.01 mol or more enables the mono-functional branched organosiloxane compound to be produced in a sufficient yield. An amount of 2.0 mol or less improves yield and enables a sufficient pot yield.

Moreover, when the inventive mono-functional branched organosiloxane compound is produced, a blending ratio of the organic chlorosilane compound and the base is not particularly limited. In view of reactivity and productivity, the reaction is preferably performed with the base in an amount of 0.1 to 6.0 mol, particularly 0.4 to 3.0 mol with respect to 1 mol of Si—Cl groups in the organic chlorosilane compound. An amount of 0.1 mol or more prevents the reaction rate from decreasing, resulting in a shorter reaction time. An amount of 6.0 mol or less enables a reaction product, the mono-functional branched organosiloxane compound, to be easily isolated, resulting in a sufficient yield.

The reaction temperature in [Step 2] preferably ranges from 1° C. to 80° C., particularly preferably 5° C. to 40° C. The reaction time preferably ranges from 30 minutes to 20 hours, particularly preferably 1 hour to 10 hours.

In [Step 2], if an amine such as ammonia is used as the base, the organic chlorosilane compound may previously react to produce an intermediate product, an organic silazane. This procedure can inhibit by-produced salts. In this procedure, the reaction temperature preferably ranges from 1° C. to 80° C., particularly preferably 5° C. to 50° C. The reaction time preferably ranges from 30 minutes to 20 hours, particularly preferably 1 hour to 10 hours.

In the case that the functional group in the general formula (1) is a silanol group, the mono-functional branched organosiloxane compound of formula (1) that contains a silanol group can be obtained by producing a branched organosiloxane compound that contains a hydrogen atom as a functional group in [Step 2] and then performing [Step 1] again.

The obtained mono-functional branched organosiloxane compound of formula (1) may be purified, for example by distillation, if necessary. The purification can be performed under normal pressure or reduced pressure according to a usual method.

When the mono-functional branched organosiloxane compound of formula (1) obtained in [Step 2] contains a hydrogen atom as the functional group, this compound can be used as the organohydrogensiloxane in [Step 1]. This enables production of a polymer compound that is more highly branched.

Illustrative examples of the mono-functional branched organosiloxane compound shown by the general formula (1) include the following structures.

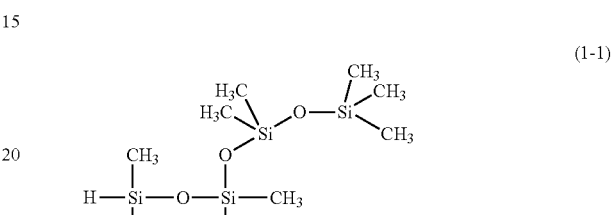

(1-1)

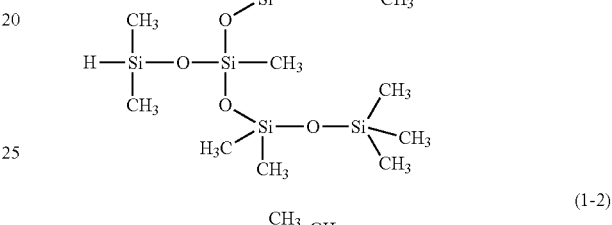

(1-2)

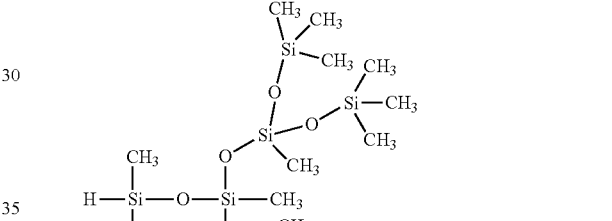

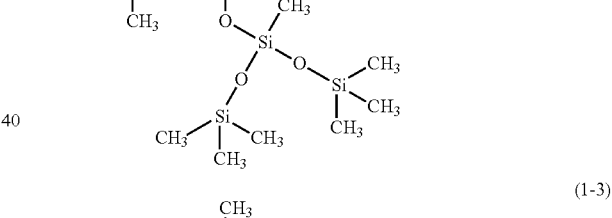

(1-3)

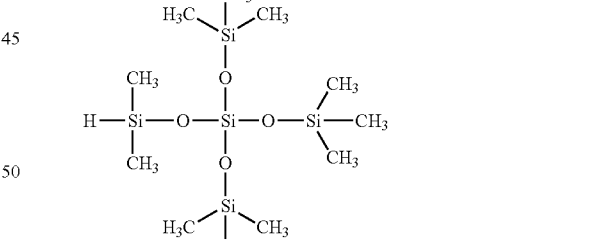

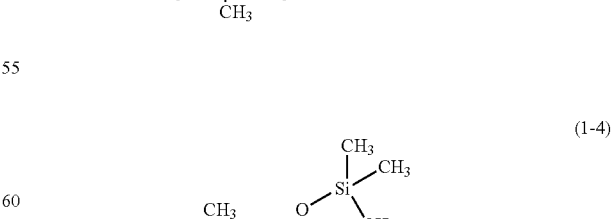

(1-4)

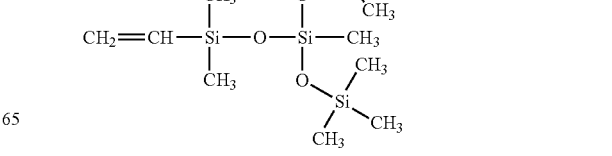

(1-5)
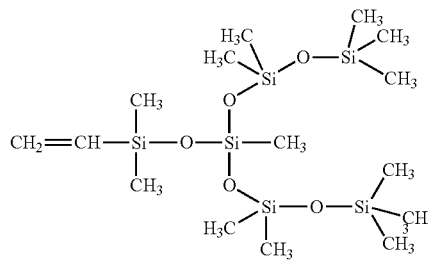

(1-6)
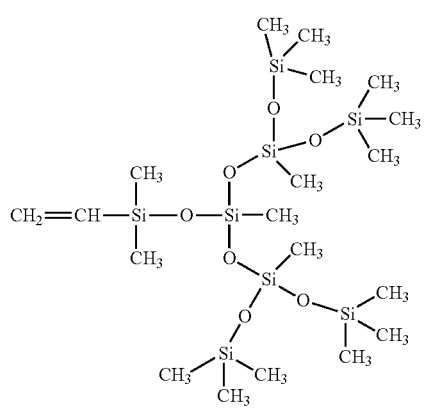

(1-7)
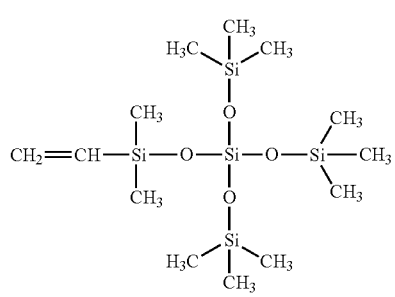

(1-8)
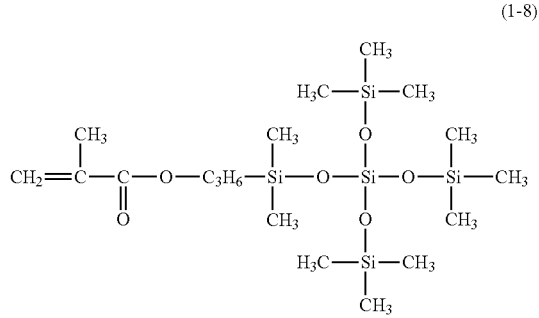

(1-9)
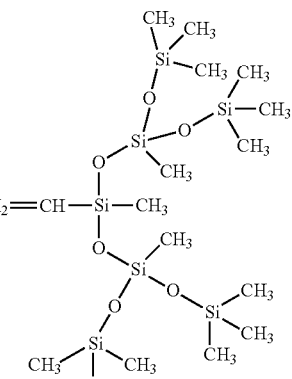

The inventive mono-functional branched organosiloxane compound can be used as a raw material of a graft organic polymer that has organosiloxane chain branches by reactivity of the functional group contained in the organosiloxane compound. The organic polymer incorporating this organosiloxane compound can give high functions such as powder dispersibility, water repellency, antifouling property, non-adhesiveness, heat resistance, wear resistance, biocompatibility, and oxygen permeability. Thus, such a compound can also be suitably used for a coating agent for electronic materials, spreader, contact lens, raw material of cosmetics, and coating material.

EXAMPLES

Hereinafter, the present invention will be more specifically described with reference to examples and comparative examples, but the present invention is not limited to the following examples. In step 1, the disappearance of Si—H and appearance of Si—OH were observed with Fourier transform infrared spectrometer (FT-IR). $^1$H-NMR analysis was performed by using deuterated chloroform as a measuring solvent, with AVANCE-III (made by Bruker BioSpin K.K.).

In the following examples, the purity of reaction product was examined by gas chromatography with a thermal conductive detector under the following condition.
Gas Chromatography (GC) Measurement Condition
Gas chromatograph: made by Agilent technologies Inc.
Detector: Flame ionization detector (FID), at 300° C. Capillary column: HP-5MS (0.25 mm×30 m×0.25 μm), made by J&W Inc.
Heating program: 50° C. (2 min)→10° C./min→250° C. (hold)
Injection port temperature: 250° C.
Carrier gas: helium (1.0 ml/min)
Split ratio: 50:1
Injection amount 1 μl Example 1

[Step 1]
A 3000-ml separable flask equipped with a stirrer, reflux condenser, dropping funnel, and thermometer was charged with 500 g of tetrahydrofuran, 122 g (6.75 mol) of water, and 0.3 g (0.00085 mol) of palladium on carbon (30 wt % on activated carbon) and cooled by ice-water bath to decrease the internal temperature to 10° C. or lower. 500 g (2.25 mol) of 1,1,1,3,5,5,5-heptamethyltrisiloxane was added dropwise thereto with an internal temperature of 5 to 10° C. The temperature was then gradually increased, and the mixture was stirred at 25° C. for 6 hours. The reaction solution was filtered through a filter, concentrated under a reduced pressure, and then distilled to obtain Compound A as a fraction having a boiling point of 91-99° C./42-43 mmHg, with a purity of 98.4%. The yield was 92%. FT-IR measurement confirmed from the disappearance of a peak at 2100 to 2200 cm$^{-1}$ and appearance of a peak at 3500 to 3700 cm$^{-1}$ that the target product was obtained.

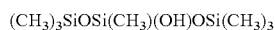

[Compound A]

[Step 2]

A 500-ml separable flask equipped with a stirrer, reflux condenser, dropping funnel, and thermometer was charged with 23.8 g (0.1 mol) of Compound A, 150 ml of n-hexane, and 10.1 g (0.1 mol) of triethylamine and cooled by ice-water bath to decrease the internal temperature to 10° C. or lower. 9.9 g (0.105 mol) of dimethylchlorosilane was added dropwise thereto with an internal temperature of 5 to 15° C., and the mixture was then stirred at 25 to 27° C. for 2 hours. The obtained reaction solution was washed with 100 g of water three times. The solvent was then distilled off by an evaporator to obtain Compound B with a purity of 99.2%. The yield was 91%.

$^1$H-NMR: 4.62 to 4.74 ppm (1H, m), −0.18 to 0.32 ppm (27H, m)

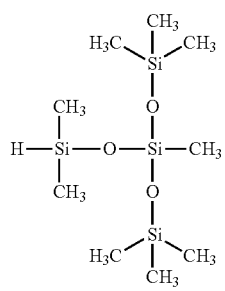

[Compound B]

Example 2

[Step 2]

A 1000-ml separable flask equipped with a stirrer, reflux condenser, dropping funnel, and thermometer was charged with 49.4 g (0.53 mol) of dimethylchlorosilane and 300 g of n-hexane and cooled by ice-water bath to decrease the internal temperature to 15° C. or lower. 27 g (1.59 mol) of ammonia was introduced into the flask to perform reaction over 2 hours. 119.3 g (0.5 mol) of Compound A was then added dropwise thereto with an internal temperature of 5 to 10° C. The mixture was stirred at 25 to 27° C. for 6 hours. The obtained reaction solution was washed with 130 g of water twice, concentrated under a reduced pressure, and then distilled to obtain Compound B as a fraction having a boiling point of 107-108° C./82 mmHg, with a purity of 97%. The yield was 85%.

$^1$H-NMR: 4.62 to 4.74 ppm (1H, m), −0.18 to 0.32 ppm (27H, m)

Example 3

[Step 2]

A 2000-ml separable flask equipped with a stirrer, reflux condenser, dropping funnel, and thermometer was charged with 303.8 g (1.28 mol) of Compound A, 500 g of n-hexane, and 124.4 g (1.23 mol) of triethylamine and cooled by ice-water bath to decrease the internal temperature to 15° C. or lower. 69 g (0.61 mol) of methyldichlorosilane was then added dropwise thereto with an internal temperature of 5 to 10° C., and the mixture was stirred at 15 to 20° C. for 12 hours. The obtained reaction solution was washed with 400 g of water twice. The solvent was then distilled off by an evaporator to obtain Compound C with a purity of 95%. The yield was 97%.

$^1$H-NMR: 4.62 to 4.74 ppm (1H, m), −0.18 to 0.32 ppm (45H, m)

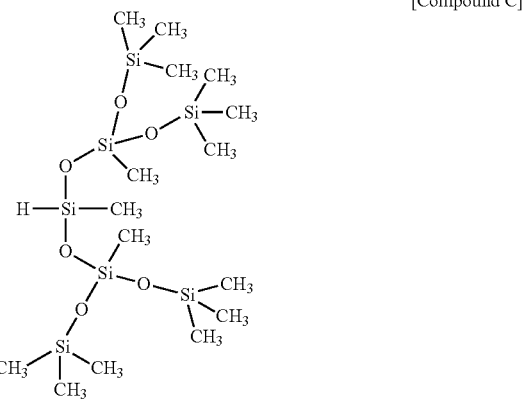

[Compound C]

Example 4

[Step 2]

A 2000-ml separable flask equipped with a stirrer, reflux condenser, dropping funnel, and thermometer was charged with 303.8 g (1.28 mol) of Compound A, 500 g of n-hexane, and 126.5 g (1.25 mol) of triethylamine and cooled by ice-water bath to decrease the internal temperature to 15° C. or lower. 85 g (0.41 mol) of 3-mercaptopropyltrichlorosilane was then added dropwise thereto with an internal temperature of 5 to 10° C., and the mixture was stirred at 15 to 20° C. for 12 hours. The obtained reaction solution was washed with 400 g of water twice. The solvent was then distilled off by an evaporator to obtain Compound D with a purity of 95%. The yield was 92%.

$^1$H-NMR: 2.40 to 2.60 ppm (2H, m), 1.65 to 1.74 ppm (2H, m), 1.25 ppm (1H, s), 0.44 to 0.55 ppm (2H, m), −0.18 to 0.32 ppm (63H, m)

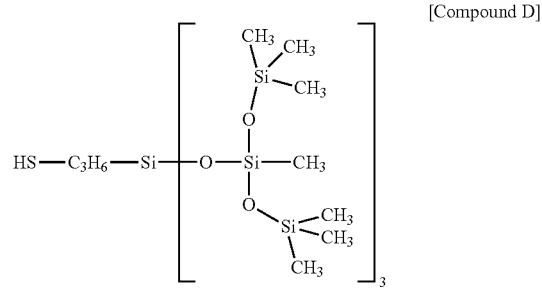

[Compound D]

Example 5

[Step 1]

A 1-L separable flask equipped with a stirrer, reflux condenser, dropping funnel, and thermometer was charged with 310 g of tetrahydrofuran, 21.6 g (1.2 mol) of water, and 527.5 g (1.02 mol) of Compound C and cooled by ice-water bath to decrease the internal temperature to 10° C. or lower. 0.0528 g (0.00015 mol) of palladium on carbon (30 wt % on activated carbon) was added thereto, and the mixture was stirred with an internal temperature of 5 to 10° C. for 1 hour. Then, the temperature was gradually increased, and the mixture was further stirred at 25° C. for 12 hours. The reaction solution was filtered through a filter, and the solvent was removed by an evaporator to obtain Compound E with a purity of 93%. The yield was 95%. FT-IR measurement confirmed from the disappearance of a peak at 2100 to 2200 $cm^{-1}$ and appearance of a peak at 3300 to 3500 $cm^{-1}$ that the target product was obtained.

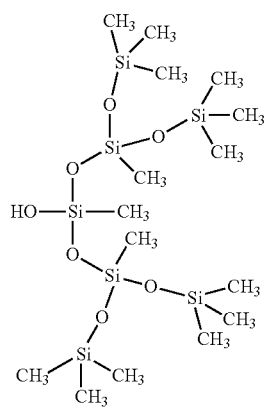

[Compound E]

[Step 2]

A 1000-ml separable flask equipped with a stirrer, reflux condenser, dropping funnel, and thermometer was charged with 107 g (0.2 mol) of Compound E, 220 ml of n-hexane, and 21.2 g (0.21 mol) of triethylamine and cooled by ice-water bath to decrease the internal temperature to 15° C. or lower. 20.9 g (0.21 mol) of dimethylchlorosilane was added dropwise thereto with an internal temperature of 5 to 15° C. The mixture was then stirred at 25 to 27° C. for 12 hours. The obtained reaction solution was washed with 50 g of water twice. The solvent was then distilled off by an evaporator to obtain Compound F with a purity of 93%. The yield was 99%.

$^1$H-NMR: 4.62 to 4.74 ppm (1H, m), −0.18 to 0.32 ppm (51H, m)

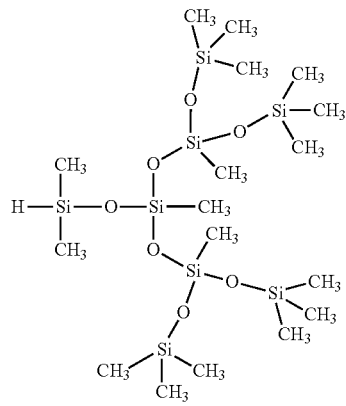

[Compound F]

Example 6

[Step 1]

A 200-ml separable flask equipped with a stirrer, reflux condenser, dropping funnel, and thermometer was charged with 64 g of tetrahydrofuran, 107 g (0.36 mol) of tris(trimethylsiloxy)silane, and 0.011 g (0.00003 mol) of palladium on carbon (30 wt % on activated carbon) and cooled by ice-water bath to decrease the internal temperature to 10° C. or lower. 9.45 g (0.525 mol) of water was added thereto, and the mixture was stirred for 1 hour with an internal temperature of 5 to 10° C. The temperature was then gradually increased, and the mixture was further stirred at 25° C. for 12 hours. The reaction solution was filtered through a filter, and the solvent was removed by an evaporator to obtain Compound G with a purity of 96%. The yield was 93%. FT-IR measurement confirmed from the disappearance of a peak at 2200 to 2300 $cm^{-1}$ and appearance of a peak at 3500 to 3700 $cm^{-1}$ that the target product was obtained.

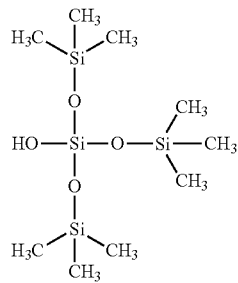

[Compound G]

[Step 2]

A 1000-ml separable flask equipped with a stirrer, reflux condenser, dropping funnel, and thermometer was charged with 71.0 g (0.23 mol) of Compound G, 313 g of n-hexane, and 24.3 g (0.24 mol) of triethylamine and cooled by ice-water bath to decrease the internal temperature to 15° C. or lower. 28.8 g (0.24 mol) of dimethylvinylchlorosilane was then added dropwise thereto with an internal temperature of 5 to 15° C., and the mixture was stirred at 20 to 23° C. for 12 hours. The reaction solution was washed with 400 g of water twice, and concentrated under a reduced pressure to obtain Compound H with a purity of 98%. The yield was 88%.

1H-NMR: 6.09 to 6.19 ppm (1H, m), 5.89 to 5.99 ppm (1H, d), 5.70 to 5.79 ppm (1H, d), −0.18 to 0.32 ppm (33H, m)

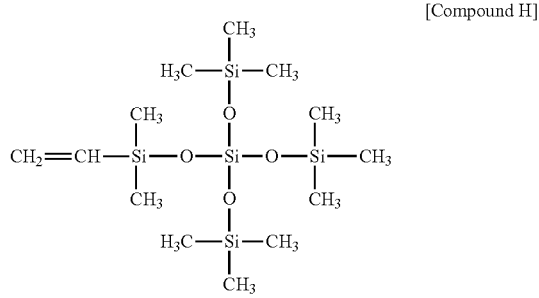 [SMILES: C=C[Si](C)(C)O[Si](O[Si](C)(C)C)(O[Si](C)(C)C)O[Si](C)(C)C]

[Compound H]

Example 7

[Step 2]

A 1000-ml separable flask equipped with a stirrer, reflux condenser, dropping funnel, and thermometer was charged with 71.0 g (0.23 mol) of Compound G, 313 g of n-hexane, and 24.3 g (0.24 mol) of triethylamine and cooled by ice-water bath to decrease the internal temperature to 15° C. or lower. 53.13 g (0.24 mol) of 3-methacryloxypropyldimethylchlorosilane was then added dropwise thereto with an internal temperature of 5 to 15° C., and the mixture was stirred at 20 to 23° C. for 12 hours. The reaction solution was washed with 400 g of water twice and mixed with 0.012 g (0.00006 mol) of dibutylhydroxytoluene, and the solvent was removed by an evaporator to obtain Compound I with a purity of 95%. The yield was 90%.

1H-NMR: 6.09 ppm (1H, s), 5.53 ppm (1H, s), 4.09 ppm (2H, t), 1.93 ppm (3H, s), 1.65 to 1.74 ppm (2H, m), 0.44 to 0.55 (2H, m), −0.18 to 0.32 ppm (33H, m)

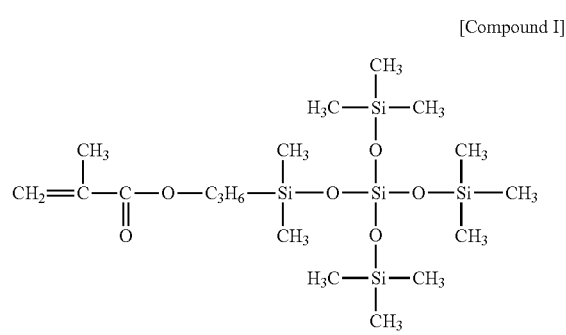

[Compound I]

Comparative Example 1

A 1000-ml separable flask equipped with a stirrer, reflux condenser, dropping funnel, and thermometer was charged with 225 g (1.0 mol) of hexamethylcyclotrisiloxane and 225 g of tetrahydrofuran and cooled by ice-water bath to decrease the internal temperature to 10° C. or lower. 270 ml (0.43 mol) of n-butyllithium (15% hexane solution, 1.6 mol/L) was added thereto, and the mixture was stirred at 5 to 10° C. for 2 hours. 23 g (0.23 mol) of triethylamine and 61.1 g (0.65 mol) of dimethylchlorosilane were added, and the reaction was performed at 40° C. for 5 hours. The reaction solution was washed with 30 g of methanol three times and distilled off under a reduced pressure to synthesize Comparative compound A. The yield was 81%.

1H-NMR: 4.62 to 4.74 ppm (1H, m), 1.25 to 1.35 ppm (4H, m), 0.85 to 0.95 ppm (3H, m), 0.50 to 0.60 ppm (2H, m), −0.18 to 0.32 ppm (42H, m)

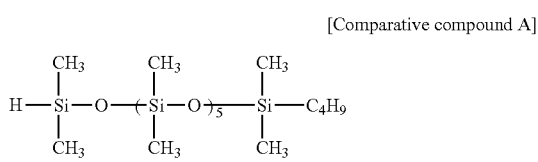

[Comparative compound A]

Comparative Example 2

A 1000-ml separable flask equipped with a stirrer, reflux condenser, dropping funnel, and thermometer was charged with 225 g (1.0 mol) of hexamethylcyclotrisiloxane and 225 g of tetrahydrofuran and cooled by ice-water bath to decrease the internal temperature to 10° C. or lower. 270 ml (0.43 mol) of n-butyllithium (15% hexane solution, 1.6 mol/L) was added thereto, and the mixture was stirred at 5 to 10° C. for 2 hours. 0.4 g (0.002 mol) of dibutylhydroxytoluene, 23 g (0.23 mol) of triethylamine, and 142 g (0.65 mol) of 3-methacryloxypropyldimethylchlorosilane were added, and the reaction was performed at 40° C. for 5 hours. The reaction solution was washed with 30 g of methanol three times, and after 0.4 g (0.002 mol) of dibutylhydroxytoluene was added, the mixture was distilled off under a reduced pressure to synthesize Comparative compound B. The yield was 80%.

1H-NMR: 6.09 ppm (1H, s), 5.53 ppm (1H, s), 4.09 ppm (2H, t), 1.93 ppm (3H, s), 1.65 to 1.74 ppm (2H, m), 1.25 to 1.35 ppm (4H, m), 0.85 to 0.95 ppm (3H, m), 0.50 to 0.60 ppm (4H, m), −0.18 to 0.32 ppm (42H, m)

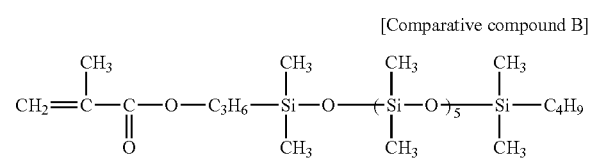

[Comparative compound B]

Examples 8 to 13 and Comparative Examples 3 and 4

Powders were treated by the following method with the formulation shown in Table 1.

TABLE 1

| Surface-treated powder | Powder | | Treatment agent | | | |
| | Particulate titanium oxide | Sericite | Compound B | Compound C | Compound F | Comparative Compound A |
|---|---|---|---|---|---|---|
| Example 8 | 98 | | 2 | | | |
| Example 9 | 98 | | | 2 | | |
| Example 10 | 98 | | | | 2 | |
| Example 11 | | 95 | 5 | | | |
| Example 12 | | 95 | | 5 | | |
| Example 13 | | 95 | | | 5 | |
| Comparative example 3 | 98 | | | | | 2 |

TABLE 1-continued

| Surface-treated powder | Powder | | Treatment agent | | | |
|---|---|---|---|---|---|---|
| | Particulate titanium oxide | Sericite | Compound B | Compound C | Compound F | Comparative Compound A |
| Comparative example 4 | | 95 | | | | 5 |

Method of Powder Surface Treatment 98 g of titanium oxide or 95 g of sericite dried under reduced pressure and subjected to heat treatment (150° C., 20 mmHg, 1 hour) was put into a reaction vessel. 2 g or 5 g of each treatment agent was diluted about 5 times with toluene, and the diluted solution was gradually added to the vessel under stirring, according to the formulation shown in Table 1. The mixture was then heated to remove toluene and further stirred at 150° C. for 3 hours.

Then, surface activity, water resistance, and hydrogen generation amount were measured on the obtained surface-treated powders. The result is given in Table 2.

TABLE 2

| Surface-treated powder | Surface activity ΔE | Water repellency (Hr) | Hydrogen generation amount (ml/g) |
|---|---|---|---|
| Example 8 | 0.8 | 2.5 | 0.6 |
| Example 9 | 0.6 | 3.0 | 0.4 |
| Example 10 | 0.4 | 4.0 | 0.3 |
| Example 11 | 0.6 | 3.0 | 0.9 |
| Example 12 | 0.3 | 3.0 | 0.6 |
| Example 13 | 0.2 | 3.5 | 0.2 |
| Comparative example 3 | 1.5 | 2.5 | 1.5 |
| Comparative example 4 | 0.9 | 3.0 | 1.2 |

Measurement Method (1) Surface activity: 40 g of treated powder and 60 g of castor oil were kneaded. A certain amount of this mixture was then interposed between quartz plates and irradiated with ultraviolet rays for a prescribed period. The color of each powder was measured before and after irradiation by a color-difference meter to examine the color difference (ΔE). The higher the surface activity of the powder, the larger the color difference.
(2) Water resistance: A certain amount of the treated powder was put into an aluminum plate (diameter: 50 mm) and then pressed. a mixed solution containing 1,3-butylene glycol and water with a ratio of 1:1 was dropped onto the central portion of the disc-shaped surface of the powder to measure time that it takes for the drop to soak and disappear into the disc. The longer this time, the higher the water resistance.
(3) Hydrogen generation amount: To measure the amount of residual Si—H, a certain amount of the powder was dispersed into toluene, and 20% KOH alkali solution was added dropwise to the dispersion. Then, generated hydrogen was collected to measure its volume.

As shown in Table 2, in case of titanium oxide, Examples 8, 9, and 10 exhibited a smaller color difference than comparative example 3; likewise, in case of sericite, Examples 11, 12, and 13 exhibited a smaller color difference than comparative example 4. This indicates that the treatment agent of the present invention (the mono-functional branched organosiloxane compound) has a lower surface activity than the linear dimethylhydrogensiloxane. Comparative examples 3 and 4 had water resistance, but generated much hydrogen, that is, unreacted Si—H groups considerably remained therein. By contrast, Examples 8 to 13 had higher water resistance and generated less hydrogen.

Example 14

A 1000-ml separable flask equipped with a stirrer, reflux condenser, dropping funnel, and thermometer was charged with 150 g of toluene and heated at 95° C. To the flask was added dropwise a mixture of 45 g of Compound I, 60 g of methyl methacrylate, 30 g of butyl methacrylate, 15 g of 2-ethylhexyl acrylate, and 4.5 g of perbutyl O (polymerization initiator, made by NOF Corporation) over 1 hour. After completion of the dropwise addition, the mixture was aged for 2 hours, followed by adding 0.5 g of perbutyl O, and heating for 3 hours. The obtained compound had a molecular weight (Mw, in terms of polystyrene) of 57,000, as measured by gel permeation chromatography (GPC).

Comparative Example 5

A 1000-ml separable flask equipped with a stirrer, reflux condenser, dropping funnel, and thermometer was charged with 150 g of toluene and heated at 95° C. To the flask was added dropwise a mixture of 45 g of Comparative compound B, 60 g of methyl methacrylate, 30 g of butyl methacrylate, 15 g of 2-ethylhexyl acrylate, and 4.5 g of perbutyl O (polymerization initiator, made by NOF Corporation) over 1 hour. After completion of the dropwise addition, the mixture was aged for 2 hours, followed by adding 0.5 g of perbutyl O, and heating for 3 hours. The obtained compound had a molecular weight (Mw, in terms of polystyrene) of 41,000, as measured by GPC.

Comparative Example 6

A 1000-ml separable flask equipped with a stirrer, reflux condenser, dropping funnel, and thermometer was charged with 150 g of toluene and heated at 95° C. To the flask was added dropwise a mixture of 70 g of methyl methacrylate, 50 g of butyl methacrylate, 30 g of 2-ethylhexyl acrylate, and 4.5 g of perbutyl O (polymerization initiator, made by NOF Corporation) over 1 hour. After completion of the dropwise addition, the mixture was aged for 2 hours, followed by adding 0.5 g of perbutyl O, and heating for 3 hours. The obtained compound had a molecular weight (Mw, in terms of polystyrene) of 21,000, as measured by GPC.

The acrylic copolymer obtained in Example 14 and Comparative examples 5 and 6 were each used to form a thin film 0.2 mm thick on a glass plate. After toluene was evaporated therefrom, sliding property and water resistance were evaluated. The result is given in Table 3.

TABLE 3

| | Sliding property | Water resistance |
|---|---|---|
| Acrylic copolymer in Example 14 | Good | Good |
| Acrylic copolymer in Comparative example 5 | Good | Slightly poor |
| Acrylic copolymer in Comparative example 6 | Poor | Poor |

Measurement Method (1) Sliding property: The surface of the thin film was touched with finger to observe sliding property.

Evaluation Criteria: Good, Slightly Poor, Poor (2) Water resistance: The plate was soaked in water and shaken by a shaker for 6 hours. Then, the state of the film was visually observed.

As shown in Table 3, the acrylic resin in Example 14 was excellent in sliding property and water resistance. The acrylic resin in Comparative example 5 exhibited excellent sliding property, but low water resistance. The acrylic resin in Comparative example 6 did not exhibit sufficient sliding property and water resistance.

It is to be noted that the present invention is not limited to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. A mono-functional branched organosiloxane compound that is liquid and shown by the following general formula (1-6):

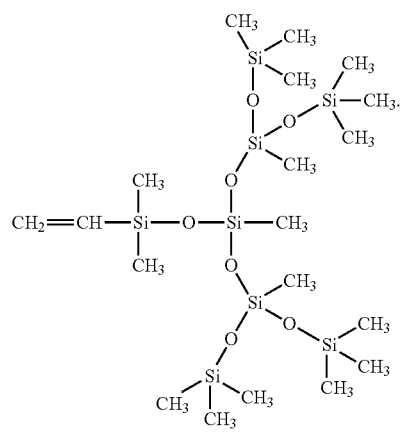

2. A method for producing a mono-functional branched organosiloxane compound of claim 1, comprising reacting an organosiloxane containing one silanol group per molecule with an organic chlorosilane compound in the presence of a base, wherein
the organosiloxane containing one silanol group per molecule is obtained by a reaction of 1,1,1,3,5,5,5-heptamethyltrisiloxane with water in the presence of a catalyst, and
the organic chlorosilane compound is dimethylvinylchlorosilane.

* * * * *